(12) United States Patent
Morawala-Patell et al.

(10) Patent No.: US 9,334,486 B2
(45) Date of Patent: May 10, 2016

(54) NITROGEN USE EFFICIENT TRANSGENIC PLANTS

(75) Inventors: Villoo Morawala-Patell, Bangalore (IN); Mahesh Venkataramaiah, Bangalore (IN); Suhas Nimbalkar, Bangalore (IN); Manjula Ramakrishna, Bangalore (IN); Suresh Sedasivam, Bangalore (IN)

(73) Assignee: Avesthagen Limited, Bangalore (IN)

( * ) Notice: Subject to any disclaimer, the term of this patent is extended or adjusted under 35 U.S.C. 154(b) by 29 days.

(21) Appl. No.: 13/054,426

(22) PCT Filed: Jul. 7, 2009

(86) PCT No.: PCT/IB2009/006226
§ 371 (c)(1),
(2), (4) Date: Apr. 2, 2011

(87) PCT Pub. No.: WO2010/007496
PCT Pub. Date: Jan. 21, 2010

(65) Prior Publication Data
US 2012/0017334 A1    Jan. 19, 2012

(30) Foreign Application Priority Data
Jul. 14, 2008  (IN) .............................. 1700/CHE2008

(51) Int. Cl.
*C12N 15/82*    (2006.01)
*C12N 9/88*    (2006.01)

(52) U.S. Cl.
CPC .............. *C12N 9/88* (2013.01); *C12N 15/8261* (2013.01)

(58) Field of Classification Search
None
See application file for complete search history.

(56) References Cited

U.S. PATENT DOCUMENTS

2007/0016976 A1*  1/2007  Katagiri et al. ............... 800/279

OTHER PUBLICATIONS

Akama and Takaiwa 2007 Journal of Experimental Botany 58: p. 2699-2707.*
Bouche and Fromme 2004 Trends in Plant Science 9:3 p. 110-115.*
Liu et al 2003 GenBank: AY187941.1.*
Yang et al 2008 (Plant Methods 4:6, p. 1-15).*

* cited by examiner

*Primary Examiner* — Brent T Page
*Assistant Examiner* — Matthew Keogh
(74) *Attorney, Agent, or Firm* — Ladas & Parry LLP

(57) ABSTRACT

The present invention relates to glutamate decarboxylase (GAD) gene sequence isolated from *Oryza sativa* (cv Rasi) and their corresponding encoded polypeptides that confer the traits of improved nitrogen use efficiency in plants. The present invention further relates to the use of these nucleic acid molecules and polypeptides in making transgenic plants, plant cells, plant materials or seeds of a plant having improved nitrogen use efficiency.

11 Claims, 17 Drawing Sheets a)

b)

c)

NITROGEN USE EFFICIENT TRANSGENIC PLANTS

FIELD OF THE INVENTION

Glutamate decarboxylase (GAD) gene sequence isolated from *Oryza sativa* and use for enhancing the nitrogen uptake and nitrogen utilization efficiency of the plants.

BACKGROUND OF THE INVENTION

Crop plants have been developed over the last 10 000 years and for most of this time they were not heavily fertilized. However, in the last 50 years the nitrogen fertilization of crop plants worldwide has increased more than 20-fold. The use of this fertilizer is generally inefficient with only about 50% being recovered in the harvested crop. Crop plants did not evolve under conditions of high nitrogen nutrition and many of the mechanisms are not necessarily suited to growth under such nutrition. The question therefore arises, can we, based on our knowledge and the experimental techniques now available to us, improve the efficiency of nitrogen use by crop plants? Two ways appear possible, one to make best use of the available variation in nitrogen use characteristics within the gene pool and, the second, to try to introduce new genes, which might increase that variation.

Increased nitrogen utilization efficiency by plants would have a number of beneficial effects. For example, nitrogen utilization efficient plants would be able to grow and yield better than conventional plants in nitrogen poor soils. The use of nitrogen efficient plants would reduce the requirement for the addition of nitrogenous fertilizers to crops. Since fertilizer application accounts for a significant percentage of the costs associated with crop production, such a reduction in fertilizer use would result in a direct monetary savings.

A reduction in fertilizer application would also lessen the environmental damage resulting from extensive nitrogenous fertilizer use. These detrimental effects of nitrogenous fertilizer use on the environment are manifested in increased eutrophication, acid rain, soil acidification, and the greenhouse effect.

PRIOR ART

Basic plant biochemistry and physiology have provided the means of better understanding of crop production systems in relation to N-supply. The interactions between carbon dioxide ($CO_2$) and nitrate ($NO_3^-$) assimilation and their dynamics are of key importance for crop production. An adequate supply of $NO_3^-$, its assimilation to amino acids (for which photosynthesized carbon compounds are required) and their availability for protein synthesis, are essential for metabolism. An adequate supply of $NO_3^-$ stimulates leaf growth and photosynthesis, the former via cell growth and division, the latter by larger contents of components of the light reactions, and those of $CO_2$ assimilation and related processes. However, the connection between metabolism and yield is poorly quantified. Biochemical characteristics and simulation models must be better used and combined to improve fertilizer-N application, efficiency of N-use, and yields. With adequate N, at full genetic potential, more C-assimilation per unit N would increase biomass.

Genetic potential may be defined as the total capacity of the plant to form biomass or yield when environmental constraints are removed; breeders and agronomists frequently refer to yield potential, although total production is more relevant when considering how the potential growth of crops may be increased. The yield potential is a function of the genetic information, which specifies the characteristics of proteins, so determining structure, growth and development, and size to which the system can grow. This maximum size over the growth cycle may be called the genetic potential.

The essential points are that when N-supply is less than required for the genetic potential to be reached, it is N uptake that must be increased to get greater biomass. Alternatively, the C-assimilation per unit of accumulated N could be increased, so that a greater biomass would result from the smaller N accumulation. Increasing genetic potential for biomass could, in theory, be achieved by increasing the C-assimilation per unit N accumulated, at the cost of increasing the C/N ratio. This assumes that adequate light energy would be available. If more N was assimilated, but without changing the balance with C-assimilation, this would theoretically increase biomass and maintain the current C/N ratio.

Plant scientists have long recognized the need to develop crops that absorb and use nutrients more efficiently. Two approaches have been used to increase nutrient use efficiency (NUE) in crop plants. The first involves both traditional breeding and marker-assisted selection in an attempt to identify the genes involved. The second uses novel gene constructs designed to improve specific aspects of NUE.

Nitrate Reductase

Two successive enzymatic steps in the nitrogen assimilation pathway reduce nitrate to ammonia. Nitrate is first converted to nitrite by nitrate reductase (NR) and then nitrite is translocated from the cytoplasm to the chloroplast, where it is reduced by nitrite reductase (NiR) to ammonium. The expression of the NR genes is influenced by several endogenous and environmental factors in plants and is highly regulated at the transcriptional, translational and post-translational levels. In summary, the over-expression of NR seems to reduce the level of nitrate in the tissue analyzed. Over-expression of either the NR or the NiR gene in plants has been shown to increase mRNA levels, and often affects N uptake. However, the increased uptake of N does not seem to increase the yield or growth of the plants regardless of the nitrogen source available. This is believed to be due, in part, to the complex regulation of NR and the pathway as a whole.

Glutamine Synthetase and Glutamate Synthase

Following the discovery of the major role of the enzyme couple glutamine synthetase (GS) and glutamate synthase (GOGAT) in ammonium assimilation in higher plants [Miflin & Lea, 1976], several laboratories have focused on understanding the mechanisms controlling the regulation of this pathway [Harrison et al., 2000]. In addition, the mutants or transgenic plants with altered levels of GS/GOGAT have been generated to determine the effects of these proteins on plant development and to study the expression of the different members of the GS multigene family. Several studies have demonstrated a direct correlation between an enhanced GS activity in transgenic plants and biomass or yield. In comparison to GS, few reports have described the production of transgenic plants over-expressing GOGAT genes. Transgenic plants over-expressing an alfalfa GOGAT gene showed an increase in GOGAT protein content but did not show any phenotype associated with this trait.

GABA Shunt

Gamma-Amino butyric acid (GABA) is a four-carbon non-protein amino acid conserved from bacteria to plants and vertebrates. GABA is a significant component of the free amino acid pool. GABA has an amino group on the gamma-carbon rather than on the alpha-carbon, and exists in an unbound form. It is highly soluble in water: structurally it is a flexible molecule that can assume several conformations in solution, including a cyclic structure that is similar to proline1. GABA is zwitterionic (carries both a positive and negative charge) at physiological pH values (pK values of 4.03 and 10.56).

It was discovered in plants more than half a century ago, but interest in GABA shifted to animals when it was revealed that GABA occurs at high levels in the brain, playing a major role in neurotransmission. Thereafter, research on GABA in vertebrates focused mainly on its role as a signaling molecule, particularly in neurotransmission. In plants and in animals, GABA is mainly metabolized via a short pathway composed of three enzymes, called the GABA shunt because it bypasses two steps of the tricarboxylic acid (TCA) cycle. The pathway is composed of the cytosolic enzyme glutamate decarboxylase (GAD) and the mitochondrial enzymes GABA transaminase (GABA-T) and succinic semialdehyde dehydrogenase (SSADH). The regulation of this conserved metabolic pathway seems to have particular characteristics in plants.

The pathway that converts glutamate to succinate via GABA is called the GABA shunt. The first step of this shunt is the direct and irreversible alpha-decarboxylation of glutamate by glutamate decarboxylase (GAD, EC 4.1.1.15). In vitro GAD activity has been characterized in crude extracts from many plant species and tissues (Brown & Shelp, 1989). GAD is specific for L-glutamate, pyridoxal 5'-phosphate-dependent, inhibited by reagents known to react with sulfhydryl groups, possesses a calmodulin-binding domain, and exhibits a sharp acidic pH optimum of ~5.8. GAD genes from *Petunia* (Baum et al., 1993), tomato (Gallego et al., 1995), tobacco (Yu & Oh, 1998) and *Arabidopsis* (Zik et al., 1998) have been identified. The second enzyme involved in the GABA shunt, GABA transaminase (GABA-T; EC 2.6.1.19), catalyzes the reversible conversion of GABA to succinic semialdehyde using either pyruvate or alpha-ketoglutarate as amino acceptors. In crude extracts, in vitro GABA-T activity appears to prefer pyruvate to alpha-ketoglutarate. However, distinct pyruvate-dependent and alpha ketoglutarate-dependent activities are present in crude extracts of tobacco leaf, and these can be separated from each other by ion exchange chromatography (Van Cauwenberghe & Shelp). Both activities exhibit a broad pH optimum from 8 to 10. The Michaelis constants (Km) of a pyruvate-specific mitochondrial GABA-T from tobacco, purified ~1000-fold, are 1.2 mM for GABA and 0.24 mM for pyruvate (Van Cauwenberghe & Shelp).

The last step of the GABA shunt is catalyzed by succinic semialdehyde dehydrogenase (SSADH; EC 1.2.1.16), irreversibly oxidizing succinic semialdehyde to succinate. The partially purified plant enzyme has an alkaline pH optimum of ~9; activity is up to 20-times greater with NAD than with NADP (Shelp et al., 1995).

Indeed, interest in the GABA shunt in plants emerged mainly from experimental observations that GABA is largely and rapidly produced in response to biotic and abiotic stresses. The GABA shunt has since been associated with various physiological responses, including the regulation of cytosolic pH, carbon fluxes into the TCA cycle, nitrogen metabolism, deterrence of insects, protection against oxidative stress, osmoregulation and signaling.

In this invention, we link these and other findings that have accumulated till date since the discovery of GABA in plants with recent evidence, mainly from *Arabidopsis* functional genomic approaches, pointing towards the possible role of GABA as a signal molecule in plants, as well as roles in plant responses to stress and in the carbon:nitrogen (C:N) balance.

SUMMARY OF THE INVENTION

The present invention relates of a method of increasing Nitrogen use efficiency in plants (monocotyledons and dicotyledons) via *Agrobacterium*-mediated transformation with a glutamate decarboxylase gene. Further more the present invention relates to a method of plant modification to express genes, related to Nitrogen use efficiency and to the plants produced using this method.

This is for the first time a method employing the glutamate decarboxylase gene to increase the nitrogen uptake and nitrogen use efficiency of plants has been demonstrated. Furthermore, genes like nitrate reductase, nitrite reductase, glutamine synthatase or glutamate dehydrogenase have been used. No attempt has been made till date to use genes involved in the GABA shunt pathway, specifically glutamate decarboxylase to increase the nitrogen use efficiency of the plants. Many studies have focused on the working of the glutamate dehydrogenase enzyme in the plants carbon nitrogen balance and nitrogen assimilation and the importance of glutamate dehydrogenase has been reviewed (Miflin & Habash 2002). However previous attempts directed at two glutamate decarboxylase genes from rice OsGAD1 and OsGAD2, which were introduced simultaneously into rice calli via *Agrobacterium* to establish transgenic cell lines produced rice plants that had aberrant phenotypes such as dwarfism, etiolated leaves, and sterility (Akama & Takaiwa, 2007).

Therefore such a need exists for efficient utilization of nitrogen when grown under low nitrogen conditions.

Sequence Listing

SEQ ID 1 shows the nucleic acid sequence of *Oryza sativa* glutamate decarboxylase gene. The start and stop codons are in italic.

SEQ ID 2 shows amino acid sequence of *Oryza sativa* glutamate decarboxylase gene. The asterisk denotes the stop codon.

BRIEF DESCRIPTION OF ACCOMPANYING FIGURES

FIG. 1 shows the plant transformation vector harboring the glutamate decarboxylase encoding DNA sequence.

FIG. 2 shows the different stages in the transformation of tobacco leaves with GAD gene through *Agrobacterium* mediated gene transfer FIG. 3 shows the PCR confirmation of the transformed and regenerated T0 seedlings of tobacco with GAD gene with different combination of primers—a) HygR-gene forward and reverse primers; b) Gene specific forward and reverse primers and c) Gene forward and Nos reverse primers.

Figure 6:
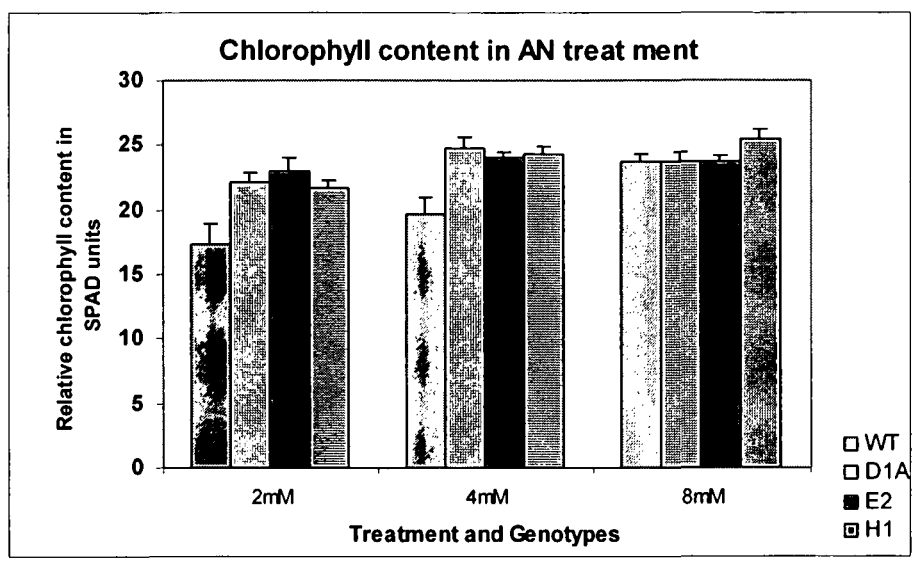

FIG. 6 shows plant N status of the T1 Seedling from three GAD transgenics (D1A, E2 and H1) grown in the green house supplemented with $1/10^{th}$ MS media without N source while N was provided separately as different concentrations of Ammonium nitrate (2, 4 and 8 mM) and were compared with the wild type for the chlorophyll content. Readings were taken using a Minolta SPAD meter and expressed as SPAD units. The values are of 5 seedlings (biological sample) and 3 readings on each seedling (experimental sample)

Figure 7:
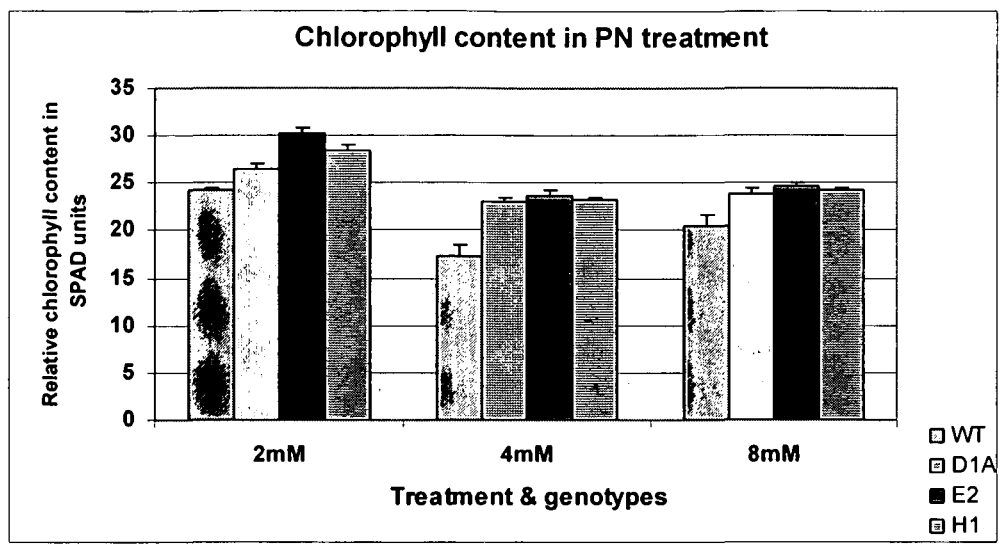

FIG. 7: shows plant N status of the T1 Seedling from three GAD transgenics (D1A, E2 and H1) grown in the green house supplemented with $1/10^{th}$ MS media without N source while N was provided separately as different concentrations of Potassium nitrate (2, 4 and 8 mM) and were compared with the wild type for the chlorophyll content. Readings were taken using a Minolta SPAD meter and expressed as SPAD units. The values are of 5 seedlings (biological sample) and 3 readings on each seedling (experimental sample)

Figure 8:
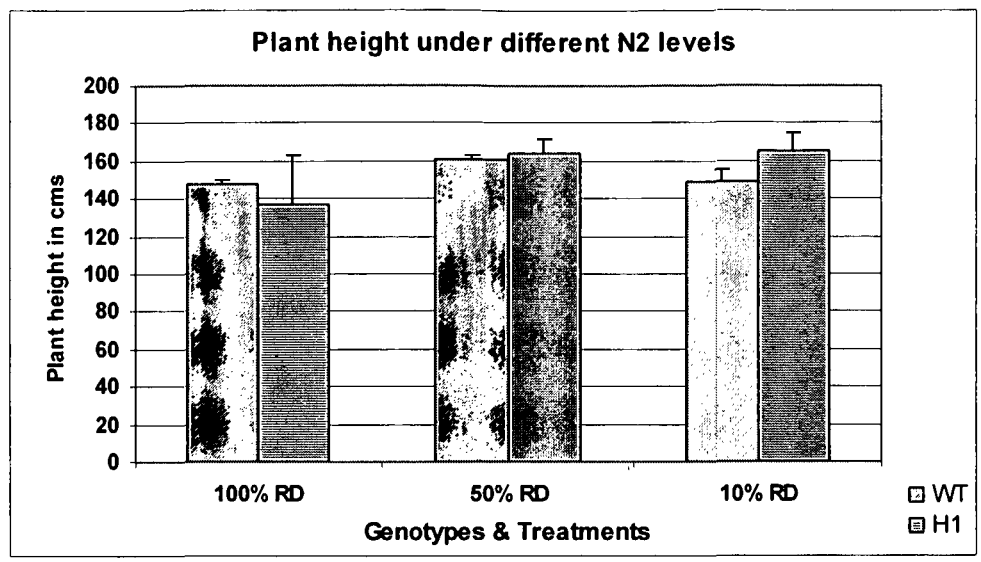

FIG. 8 shows comparison of plant height between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 9:
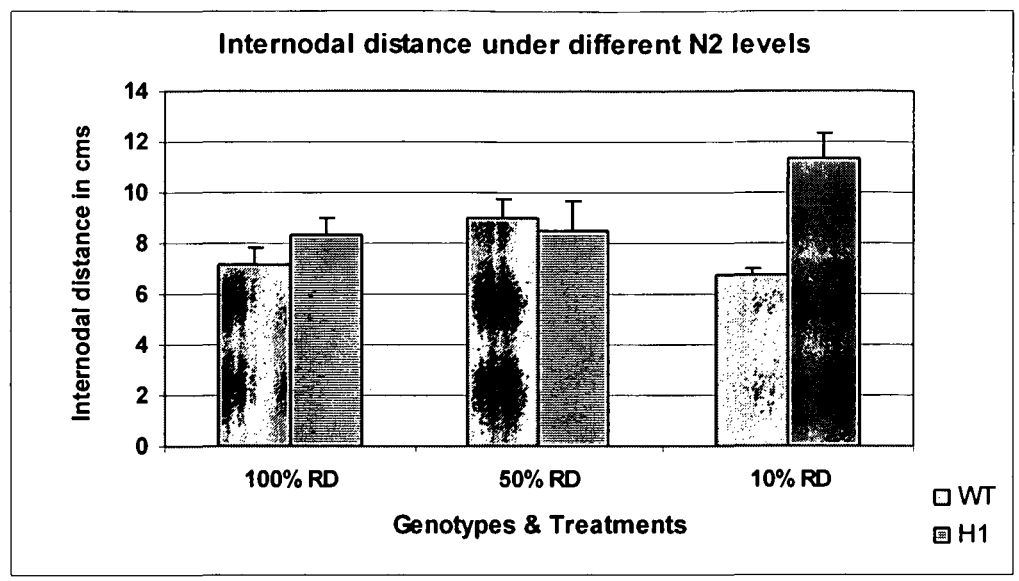

FIG. 9 shows comparison of internodal distance between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 10:
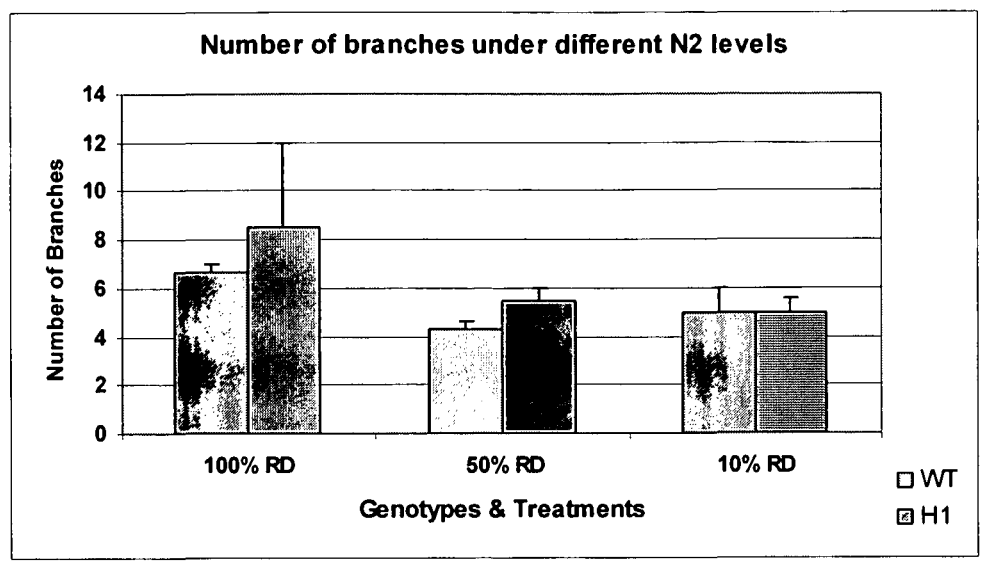

FIG. 10 shows comparison of number of branches between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 11:
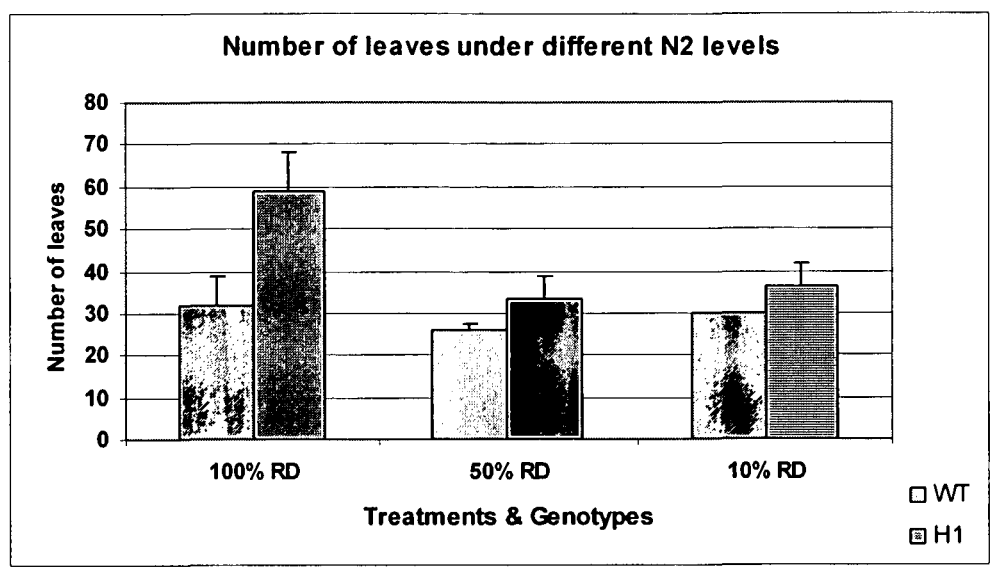

FIG. 11 shows comparison of number of leaves between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 12:
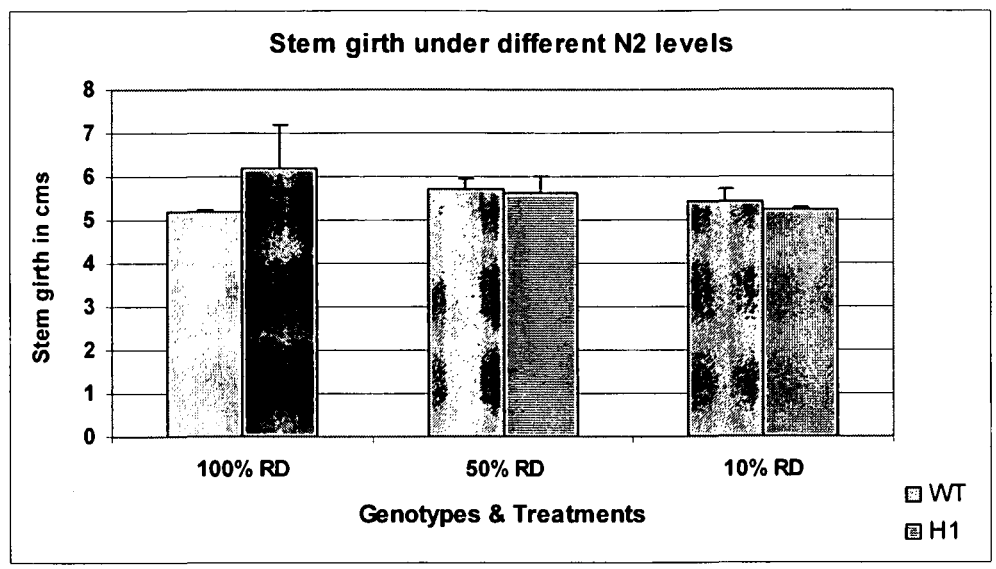

FIG. 12 shows comparison of stem girth between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 13:
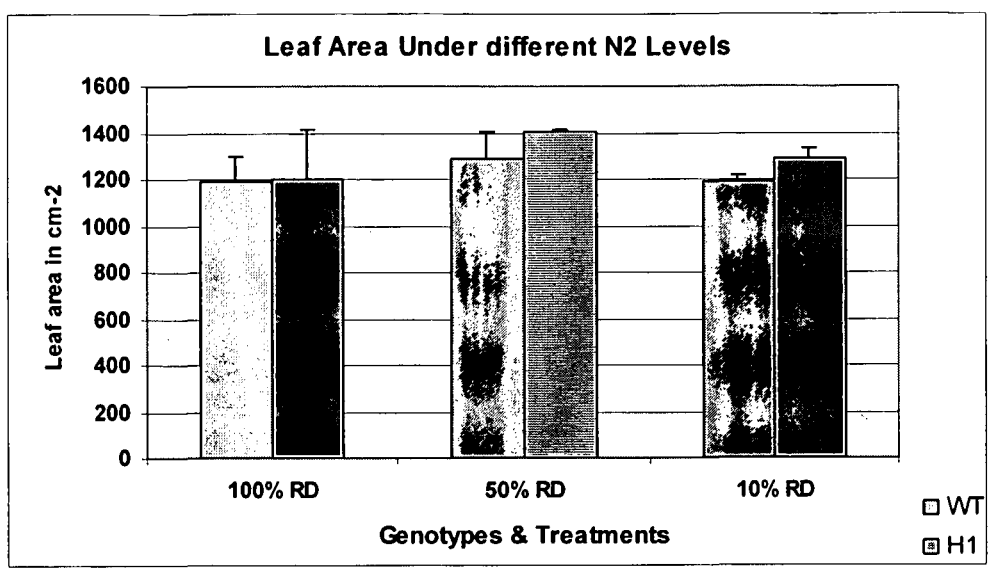

FIG. 13 shows comparison of leaf area between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 14:
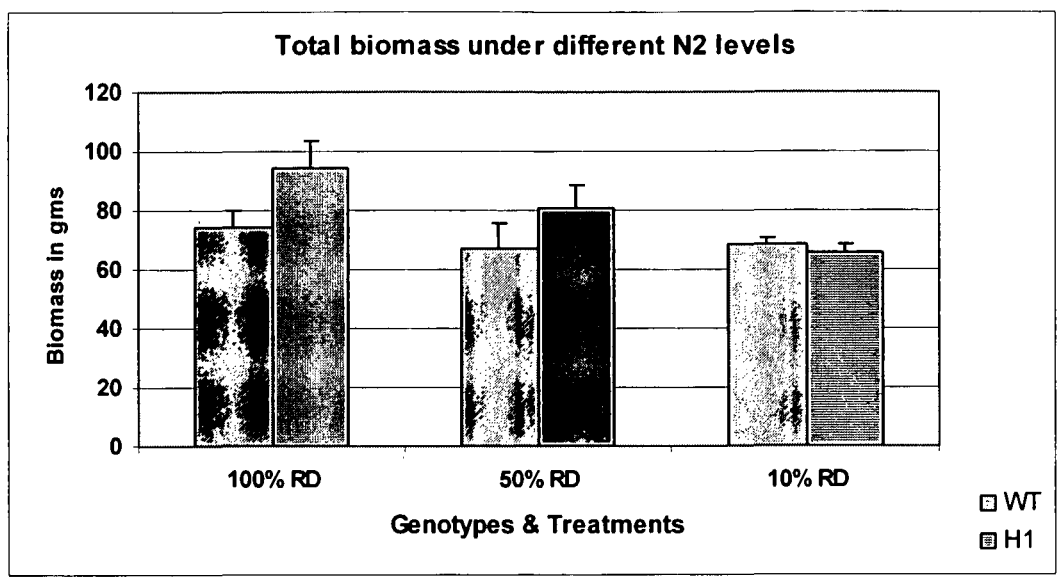

FIG. 14 shows comparison of total biomass (Leaves, stems and roots) on dry weight basis between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 15:
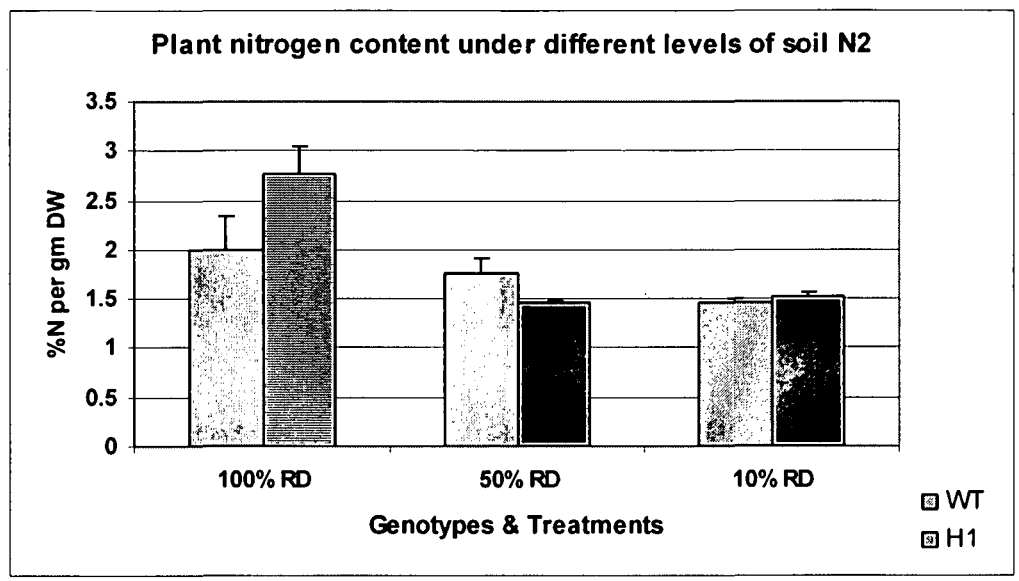

FIG. 15 shows comparison of total N % in the leaves on unit dry weight basis between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

Figure 16:
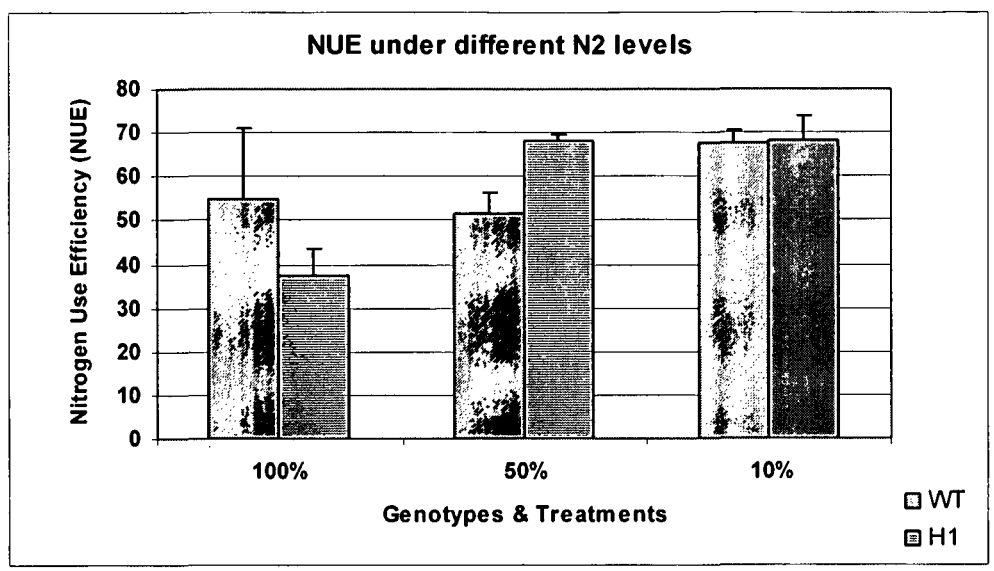

FIG. 16 shows comparison of Nitrogen use efficiency (NUE) on unit dry weight basis, which was calculated as biomass/amount of N in biomass between T1 Seedlings from GAD transgenic (H1) which were positive for Hygromycin resistance, and the wild type seedlings when grown in pots in the green house with different levels of N fertilizer (100% Recommended dose (RD), 50% RD and 10% RD) and constant levels of P and K fertilizers.

Figure 17:
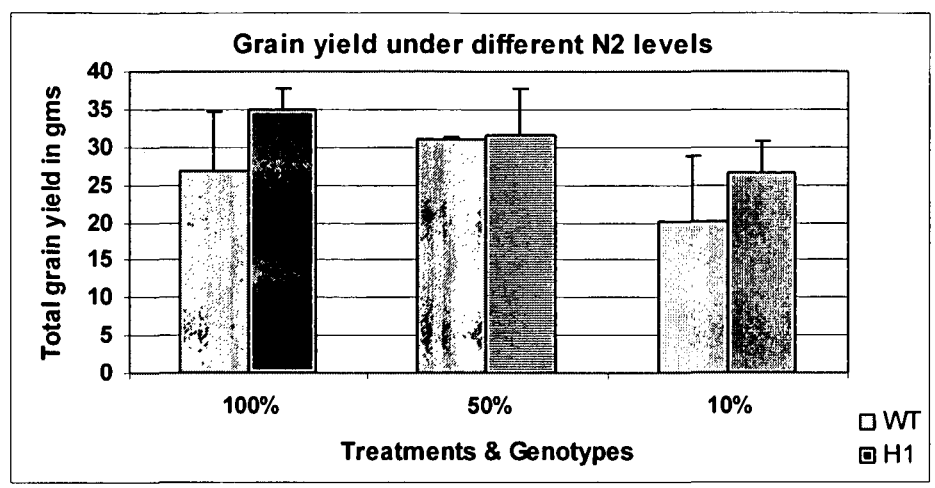

FIG. 17: shows comparison of total grain yield between T1 Seedlings from GAD transgenic (H1) which were positive for Hygromycin resistance and the wild type seedlings when grown in pots in the green house with different levels of N fertilizer (100% Recommended dose (RD), 50% RD and 10% RD) and constant levels of P and K fertilizers.

DETAILED DESCRIPTION OF THE INVENTION

The following detailed description of the invention is provided to aid those skilled in the art in practicing the present invention. Even so, the following detailed description of the invention should not be construed to unduly limit the present invention as modifications and variations in the embodiments discussed herein may be made by those of ordinary skill in the art without departing from the spirit or scope of the present invention.

This invention relates to a purified and isolated DNA sequence having characteristics of glutamate decarboxylase.

According to the present invention, the purified and isolated DNA sequence usually consists of a glutamate decarboxylase nucleotide sequence or a fragment thereof.

Included in the present invention are as well complementary sequences of the above-mentioned sequences or fragment, which can be produced by any means.

Encompassed by this present invention variants of the above mentioned sequences, that is nucleotide sequences that vary from the reference sequence by conservative nucleotide substitutions, whereby one or more nucleotides are substituted by another with same characteristics.

According to the present invention, the above mentioned nucleotide sequences could be located at both the 5' and the 3' ends of the sequence containing the promoter and the gene of interest in the expression vector.

Included in the present invention are the use of above mentioned sequences in increasing the nitrogen use efficiency of the plants produced thereof. "Nitrogen use efficiency" means that after introduction of DNA sequence under suitable conditions into a host plant, the sequence is capable of enhancing nitrogen levels in the plants as compared to control plants where the plants are not transfected with the said DNA sequence.

The following definitions are used in order to help in understanding the invention.

"Chromosome" is organized structure of DNA and proteins found inside the cell.

"Chromatin" is the complex of DNA and protein, found inside the nuclei of eukaryotic cells, which makes up the chromosome.

"DNA" or Deoxyribonucleic Acid, contain genetic informations. It is made up of different nucleotides.

A "gene" is a deoxyribonucleotide (DNA) sequence coding for a given mature protein. "gene" shall not include untranslated flanking regions such as RNA transcription initiation signals, polyadenylation addition sites, promoters or enhancers.

"Promoter" is a nucleic acid sequence that controls expression of a gene.

"Enhancer" refers to the sequence of gene that acts to initiate the transcription of the gene independent of the position or orientation of the gene.

The definition of "vector" herein refers to a DNA molecule into which foreign fragments of DNA may be inserted. Vectors, usually derived from plasmids, functions like a "molecular carrier", which will carry fragments of DNA into a host cell.

"Plasmid" are small circles of DNA found in bacteria and some other organisms. Plasmids can replicate independently of the host cell chromosome.

"Transcription" refers the synthesis of RNA from a DNA template.

"Translation" means the synthesis of a polypeptide from messenger RNA.

"Orinetation" refers to the order of nucleotides in the DNA sequence.

"Gene amplification" refers to the repeated replication of a certain gene without proportional increase in the copy number of other genes.

"Transformation" means the introduction of a foreign genetic material (DNA) into plant cells by any means of transfer. Different method of transformation includes bombardment with gene gun (biolistic), electroporation, *Agrobacterium* mediated transformation etc.

"Transformed plant" refers to the plant in which the foreign DNA has been introduced into the said plant. This DNA will be a part of the host chromosome.

"Stable gene expression" means preparation of stable transformed plant that permanently express the gene of interest depends on the stable integration of plasmid into the host chromosome.

While the invention is broadly as defined above, it will be appreciated by those persons skilled in the art that it is not limited thereto and that it also includes embodiments of which the following description gives examples.

Example 1

Isolation and Purification of GAD Gene Nucleotide Sequence from Rice and Construction of Plant Transformation Vector The GAD gene is cloned downstream of a 35S cauliflower mosaic virus promoter and terminated with a NOS terminator, all operably linked.

Plant Materials

*Oryza sativa* (cv Rasi) was used for preparation of nucleic acids. After germination of the seeds, they were grown in hydroponic solution in a culture room. The seedlings were treated with 150 mM NaCl for 7-16 h.

RNA Extraction and EST Library Construction

The RNA was extracted from the whole seedlings. An EST library of the salt stressed Rasi cDNA was constructed. An EST showing identity to glutamate decarboxylase was identified from the EST library.

Identification and Isolation of Genes in the GABA Shunt

GABA accumulates in higher plants following the onset of a variety of stresses such as acidification, oxygen deficiency, low temperature, heat shock, mechanical stimulation, pathogen attack, drought and salt stress. Glutamate decarboxylase, the gene in the GABA shunt has been isolated from the salt stressed library of *O. sativa*.

Cloning of Glutamate Decarboxylase Gene

The Glutamate decarboxylase gene has been cloned into a cloning vector and also into plant transformation vectors (biolistic and binary) under a constitutive promoter. The cDNA encoding the complete coding sequence of glutamate decarboxylase gene was amplified from the indica rice (cv. Rasi) cDNA using the following pairs of primers tagged with BglII and EcoRI restriction enzyme sites (underlined nucleotide sequences)

```
Forward:  5'-GCGGATCCATGGTGCTCTCCAAGGCCGTCTC-3'

Reverse:  5'-GCGAATTCCTAGCAGACGCCGTTGGTCCTCTTG-3'
```

Using the following PCR conditions 94° C. for 1 min; 94° C. for 30 sec; 75° C. for 3 min (cycled for five times); 94° C. for 30 sec; 68° C. for 3 min (cycled for 30 times) with a final extension of 68° C. for 7 min.

The amplified cDNA consists of 1479 base pairs of nucleotides and encodes for a mature glutamate decarboxylase enzyme.

The amplified fragment was cloned into pGEMT easy vector. The gene was restriction digested at BamHI and EcoRI sites and ligated into a biolistic vector pV1. This biolistic vector was excised at BglII and EcoRI restriction sites (BglII and BamHI enzymes generate compatible ends) to confirm the presence of the gene. The gene was also confirmed by sequencing. The resultant vector (pV1-GAD) has the GAD gene (1.479 kb) driven by 35S Cauliflower Mosaic virus (35S CaMV) promoter and NOS terminator along with the ampicillin resistance gene as a selectable marker.

Figure 1:
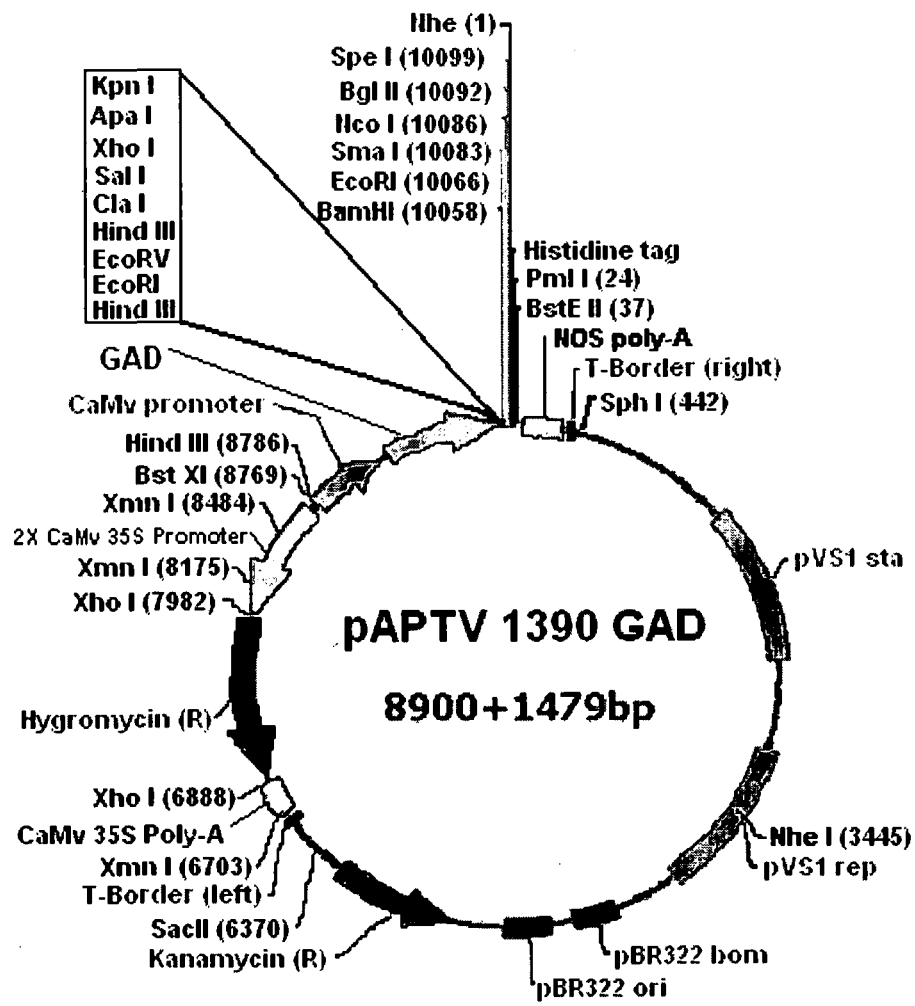

The gene cassette, GAD gene driven by the 35S CaMV promoter and terminated by the NOS terminator from pV1-GD was restriction digested at HindIII and BamHI sites. This gene cassette was ligated into pCAMBIA 1390 pNG15 which was restriction digested at HindIII and BamHI sites. The resultant vector (pAPTV 1390-GAD) has the GAD gene (1.479 kb) driven by 35S cauliflower mosaic virus (35S CaMV) promoter and terminated by NOS terminator along with the nptII (Kanamycin resistance) gene and hph gene (Hygromycin resistance) as selectable markers (FIG. 1).

Example 2

Generating Plants with an Altered GAD Gene and Having Higher N Content

Plant Transformations

The Glutamate decarboxylase gene has been transformed via *Agrobacterium* into tobacco (model plant) to arrive at the proof of concept for the identified gene.

Figure 2:
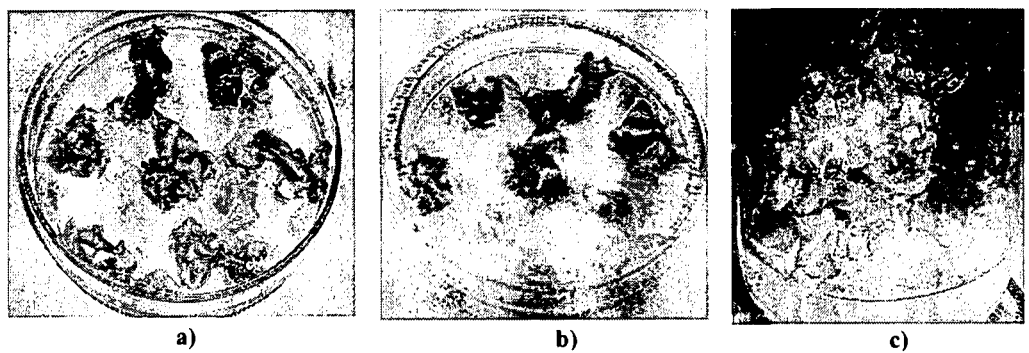

Detailed Steps Involved in *Agrobacterium* Mediated Transformation of Tobacco Leaf Explants with a Binary Vector Harboring GAD Gene:

1. The positive colony of *Agrobacterium* was inoculated in to LB broth with 50 mg/L Kanamycin (Kan) and 10 mg/L of Rifamicin (Rif) as vector backbone consists of Kan and Rif resistance gene, which also functions as double selection at one shot.
2. Then the broth was incubated at 28° C. on a shaker.
3. The overnight grown colony was inoculated into 50 mL LB broth with 50 mg/L Kan and 10 mg/L of Rif in the morning and incubated at 28° C. for 3-4 hours and the OD was checked at 600 nm and continued to grow till the OD was between 0.6-1.
4. Once the broth reached required OD the broth was centrifuged at 5000 rpm for 5 min.
5. The supernatant was discarded and the cell pellet was dissolved in Murashige & Skooge (MS) liquid medium (Agro-MS broth).
6. The tobacco leaves were cut in to small square pieces which served as explants with out taking the midrib and care was taken to injure leaf at all four sides with out injuring much at the center part of the inoculants.
7. These leaf samples were placed in MS Plain media for two days in a BOD incubator. After two days of inoculation these leaf samples were infected with transformed *Agrobacterium* cells, which are now in Agro-MS broth.
8. The leaf explants were placed in this Agro-MS broth for 30 min and then placed them on co-cultivation media, which consist of MS+1 mg/L 6-Benzyl amino purine hydrochloride (BAP)+0.2 mg/L Naphthalene acetic acid (NAA)+250 mg/L Cefotaxime for two days (FIG. 2a)
9. After co-cultivation the explants were kept in first selection medium which consist of MS+1 mg/L BAP+0.2 mg/L NAA+40 mg Hyg+250 mg/L Cefotaxime for 15 days and as the callus started protruding these explants were again sub cultured on to first selection media for callus to mature enough (FIG. 2b)
10. Once the callus was found to be matured these callus were inoculated on to second selection medium which consist of MS+1 mg/L BAP+0.2 mg/L NAA+50 mg Hyg+250 mg/L Cefotaxime. As the concentration of Hygromycin is increased the escapes from first selection get suppressed and only the transformed callus starts surviving on this media.
11. Subsequent sub-cultures on this second selection media were done once in ten days.
12. By this time the plantlets started protruding from the callus. The plantlets from second selection were taken and placed on to rooting media, which consist of ½ MS+0.2 mg/L Indole-3-butyric acid (IBA). Here the plantlets started protruding roots by 12-15 days. Once the mature roots were formed the plants were subcultured on to rooting media along with 20 mg/L of Hygromycin, as escapes can be identified at this stage also (FIG. 2c).
13. Plants at this stage were subjected to acclimatization where the caps of bottles were kept open for two days so that plants get adjusted to its growth room environment. Later plants from agar medium were removed and placed on ¼ MS liquid medium for two days. These plants were further transferred on to vermiculate and watered every day for one week.
14. Depending upon the condition of the plants suitable plants were transferred to green house.
15. Before sending plants to green house during acclimatization period old leaves from the plants were collected.
16. DNA from respective leaf samples was extracted and PCR with gene specific primers and selection marker gene i.e. Hygromycin primers were performed. PCR confirmed positive plants were further transferred to green house.

Confirmation of Plants with Introduced GAD Gene
Genomic DNA Extraction of GAD Tobacco Transgenic Lines Leaf samples of transgenic GAD tobacco plant were collected and genomic DNA was extracted.

Procedure for Genomic DNA Extraction:
Around 1 gm of leaf was collected from each plant.
The samples were ground using liquid nitrogen in a pestle and mortar.
1 ml of extraction buffer Extraction buffer (0.2M Tris Cl pH-8.0; 2 M NaCl; 0.05 M EDTA; 2% CTAB) was added to the sample and spun at 13000 rpm for 10 min
Supernatant was collected. RNase [3 µl (1 mg/mL) for 1 ml] was added and incubated at 37° C. for ½ an hour.
Equal volumes of chloroform-isoamyl alcohol was then added and spun at 13000 rpm for 10 min. Supernatant was collected in fresh tubes and equal volumes of chilled Isopropanol was added and spun at 13000 rpm for 10 min.
The pellet was washed with 70% alcohol and pellet was dried and dissolved in 30 µl warm autoclaved water.
1 µl of DNA was loaded and checked on gel.

The Transgenic Plants were Confirmed by PCR with Different Combination of Primers:
1. PCR with Hygromycin Forward (Hyg F) & Hygromycin Reverse (Hyg R) primers:

| Reagent | Stock | Volume |
| --- | --- | --- |
| Template DNA | | 1 µl |
| Hyg F | 10 pM | 0.5 µl |
| Hyg R | 10 pM | 0.5 µl |
| dNTP's | 10 mM | 0.5 µl |
| Taq DNA polymerase | 3 U/µl | 0.3 µl |
| Taq buffer A | 10X | 3 µl |
| Milli Q water | | 24.2 µl |
| Total volume | | 30 µl |

PCR Conditions: (Eppendorf Machine)

| Steps | Temperature | Time | Cycle |
| --- | --- | --- | --- |
| 1 | 94° C. | 3 mins | |
| 2 | 94° C. | 30 secs | |
| 3 | 50° C. | 50 secs | |
| 4 | 72° C. | 1 min | Go to step-2 30X |
| 5 | 72° C. | 10 mins | |
| 6 | 10° C. | ∞ | |

Figure 3:
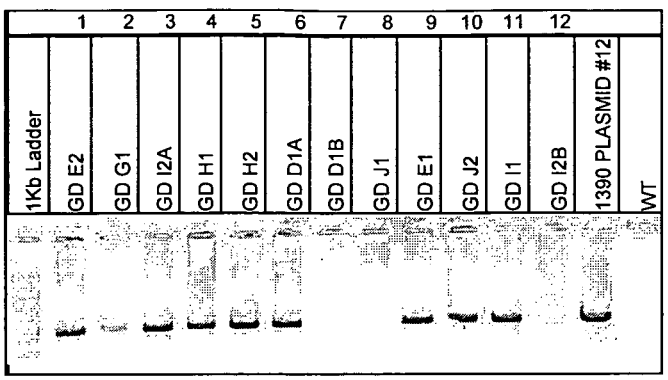
Figure 3:
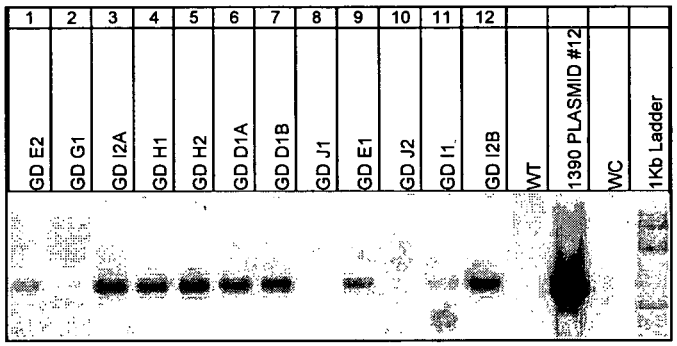
Figure 3:
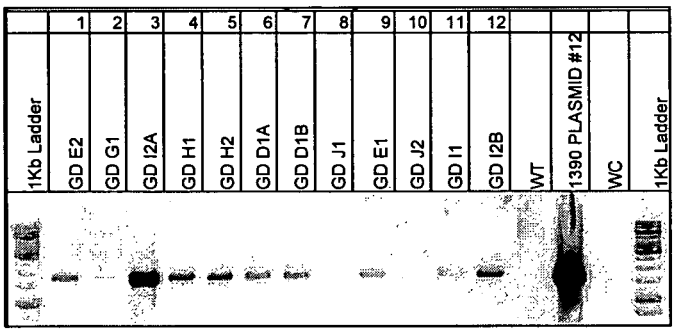

The amplified product was visualized on 0.8% agarose gel shown in FIG. 3a.

2. PCR with Gene specific primers GAD Forward (GD F) & GAD Reverse (GD R):

| Reagent | Stock | Volume |
| --- | --- | --- |
| Template DNA | | 2 µl |
| GD F | 10 pM | 0.5 µl |
| GD R | 10 pM | 0.5 µl |
| dNTP's | 10 mM | 0.5 µl |
| Taq DNA polymerase | 3 U/µl | 0.3 µl |
| Taq buffer A | 10X | 2 µl |
| Milli Q water | | 14.2 µl |
| Total volume | | 20 µl |

PCR Conditions: (Eppendorf Machine)

| Steps | Temperature | Time | Cycle |
| --- | --- | --- | --- |
| 1 | 94° C. | 3 mins | |
| 2 | 94° C. | 30 secs | |
| 3 | 69° C. | 50 secs | |
| 4 | 72° C. | 1.30 min | Go to step-2 35X |
| 5 | 72° C. | 10 mins | |
| 6 | 10° C. | ∞ | |

The amplified product was visualized on 0.8% agarose gel (FIG. 3b)

3. PCR with GD F & Nos MR:

| Reagent | Stock | Volume |
| --- | --- | --- |
| Template DNA | | 2 µl |
| GD F | 10 pM | 0.5 µl |
| Nos MR | 10 pM | 0.5 µl |
| dNTP's | 10 mM | 0.5 µl |
| Taq DNA polymerase | 3 U/µl | 0.3 µl |
| Taq buffer A | 10X | 2 µl |
| Milli Q water | | 14.2 µl |
| Total volume | | 20 µl |

PCR Conditions: (Eppendorf Machine)

| Steps | Temperature | Time | Cycle |
|---|---|---|---|
| 1 | 94° C. | 3 mins | |
| 2 | 94° C. | 30 secs | |
| 3 | 67° C. | 50 secs | |
| 4 | 72° C. | 2 min | Go to step-2 35X |
| 5 | 72° C. | 10 mins | |
| 6 | 10° C. | ∞ | |

The amplified product was visualized on 0.8% agarose gel shown in FIG. 3c.

Primer sequences used in different PCR reactions are listed below:

Hyg F:    5'-CTGAACTCACCGCGACGTCT-3'

Hyg R:    5'-CCACTATCGGCGAGTACTTC-3'

GD F:     5'-GCGGATCCATGGTGCTCTCCAAGGCCGTCTC-3'

GD R:     5'-GCGAATTCCTAGCAGACGCCGTTGGTCCTCTTG-3'

NOS MR:   5'-GATAATCATCGCAAGACCGGCAAC-3'

Confirmation of Expression of the Introduced GAD Gene in the Transgenic Plants

The confirmation of the expression of the introduced GAD gene involved steps like RNA extraction, cDNA synthesis and Reverse Transcription PCR.

RNA of transgenic GAD tobacco plants along with the control plant (wild type) was isolated.

Detailed Steps Involved in RNA Extraction:
1. 500 mg of leaf tissue was taken in prechilled mortar and ground in liquid nitrogen to fine powder.
2. The powder was transferred to a prechilled eppendorf tube using a chilled spatula.
3. 1 ml of Trizol solution (Invitrogen) was added to the homogenized sample. Mixed well and incubated at room temperature (RT) for 5 min.
4. 200 μl of chloroform was added to it and shaken vigorously for 15 seconds and incubated at room temperature for 5 mins.
5. The samples were centrifuged at 13000 rpm for 15 min at 4° C.
6. The upper aqueous phase was collected in a fresh tube (Approximately 60% i.e. 600 μl)
7. 500 μl of cold Isopropanol was added to the upper phase collected and incubated at RT for 10 min.
8. The samples were centrifuged at 13000 rpm for 15 min at 4° C.
9. The supernatant was decanted and the pellet washed with 500 μl of 70% alcohol (DEPC $H_2O$) and centrifuged at 10000 rpm for 5 minutes at 4° C.
10. The supernatant was decanted and the pellet dried for 15 min at RT.
11. The pellet was dissolved in 20 μl of DEPC treated $H_2O$ in a heating water bath or dry bath set at 55° C.
12. 2 μl of the sample is loaded on the gel. Stored the sample at −80° C. till further use.

Detailed Steps Involved in cDNA Synthesis:
cDNA synthesis of transgenic GAD tobacco plants along with the wild type was done.

1. The components were added in the order given below:

| | |
|---|---|
| Total RNA | 4 ul (1 ug) |
| Oligo dT's | 0.5 ul |
| 0.1% DEPC/nuclease free water | 6.5 ul |
| Total | 11 ul |

2. The contents were heated at 70° C. for 5 min in a PCR machine and snap chilled in ice.
3. Meanwhile the next mixture was prepared by adding the following components in another tube:

| | |
|---|---|
| 5x reaction buffer | 4 ul |
| dNTP's (10 mM) | 2 ul |
| RNase inhibitor (20 U/ul) | 0.5 ul |
| 0.1% DEPC/nuclease free water | 2 ul |
| Total | 8.5 ul |

4. This 8.5 ul mixture was added to the content in PCR tube, which was snap chilled and mixed by gentle tapping.
5. The contents were incubated in PCR tube at 37° C. for 5 minutes in a PCR machine.
6. 0.5 ul of the M-MuLV RT enzyme was added to the tube and continued the program set in the PCR machine (25° C. for 10 min; 37° C. for 60 min and 70° C. for 10 min).
7. Store the cDNA at −20° C. till further use in PCRs.

Analysis of Expression of the Introduced GAD Gene in the Transgenic Tobacco Plants by RT-PCR The cDNA samples from GAD transgenic tobacco and wild type plant were analyzed by PCR with Gene specific primers to check for the expression of the introduced GAD gene in tobacco:

PCR of cDNA with Gene Specific Primers:

| Reagent | Stock | Volume |
|---|---|---|
| Template cDNA (1:10) | | 2 μl |
| GD F | 10 pM | 0.5 μl |
| GD R | 10 pM | 0.5 μl |
| dNTP's | 10 mM | 0.5 μl |
| Taq DNA polymerase | 3 U/μl | 0.3 μl |
| Taq buffer A | 10X | 3 μl |
| Milli Q water | | 24.2 μl |
| Total volume | | 30 μl |

PCR Conditions (Eppendorf Machine):

| Steps | Temperature | Time | Cycle |
|---|---|---|---|
| 1 | 94° C. | 3 mins | |
| 2 | 94° C. | 30 secs | |
| 3 | 69° C. | 50 secs | |
| 4 | 72° C. | 1.30 min | Go to step-2 30X |
| 5 | 72° C. | 10 mins | |
| 6 | 10° C. | ∞ | |

Figure 4:
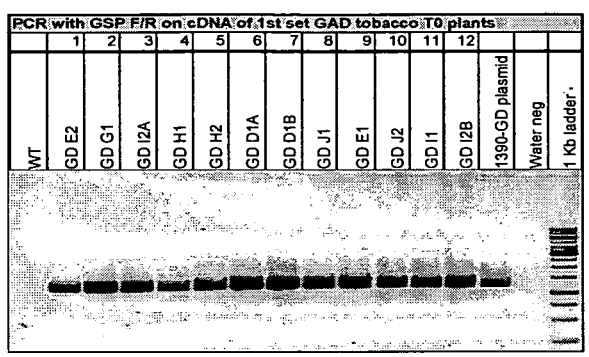
FIG. 4 shows the confirmation of the expression of the introduced gene (GAD) in T0 seedlings of tobacco with GAD gene analyzed using RT-PCR on cDNA as template with GAD gene specific forward and reverse primers.

The amplified product was visualized on 0.8% agarose gel as shown in FIG. 4.

Nitrogen Estimation in T0 Plants

Analysis of T0 GAD tobacco plants along with the wild type was done for the nitrogen content in the leaves. The leaves were collected from mature plants and dried in hot air oven. The dried leaves were powdered and the $N_2$ content was estimated using Kjeldahl method. The Kjeldahl method is the standard method of nitrogen determination. The method consists of three basic steps: 1) digestion of the sample in sulfuric acid with a catalyst, which results in conversion of nitrogen to ammonia; 2) distillation of the ammonia into a trapping solution; and 3) quantification of the ammonia by titration with a standard solution.

Procedure

Digestion

1. Approximately 0.200 g ground leaf sample was weighed into digestion flask, recording weight (W) to nearest 0.1 mg.
2. 3.5 g of the digestion mixture was added and then 10 ml of sulfuric acid. Placed the flask on preheated burner of BIOKJEL at 42° C.
3. The tubes of the BIOSCRUB unit were connected to the digestion flask to collect the fumes while heating.
4. The mixture in the tube/flask was heated for about 60-90 mins until the digestion mixture has turned light green in colour.
5. After digestion, the digestion tubes were placed on the stand for cooling.

Distillation and Titration

1. Transferred the digestion tube in the distillation apparatus, BIODIST, the conical flask on the receiving end and run the distillation.
2. The contents of the conical flask were titrated with 0.1N HCL until the appearance of the pale permanent pink colour.

Calculation

Percent Nitrogen (N) was calculated as $$\% N = \frac{[S - B] \times 0.1 \times 14 \times 100}{W \times 1000}$$

Where

S=Titre value for sample; B=Titre value for blank; 14=Equivalent weight of Nitrogen; 0.1=Normality of HCL; W=sample weight in grams.

Figure 5:
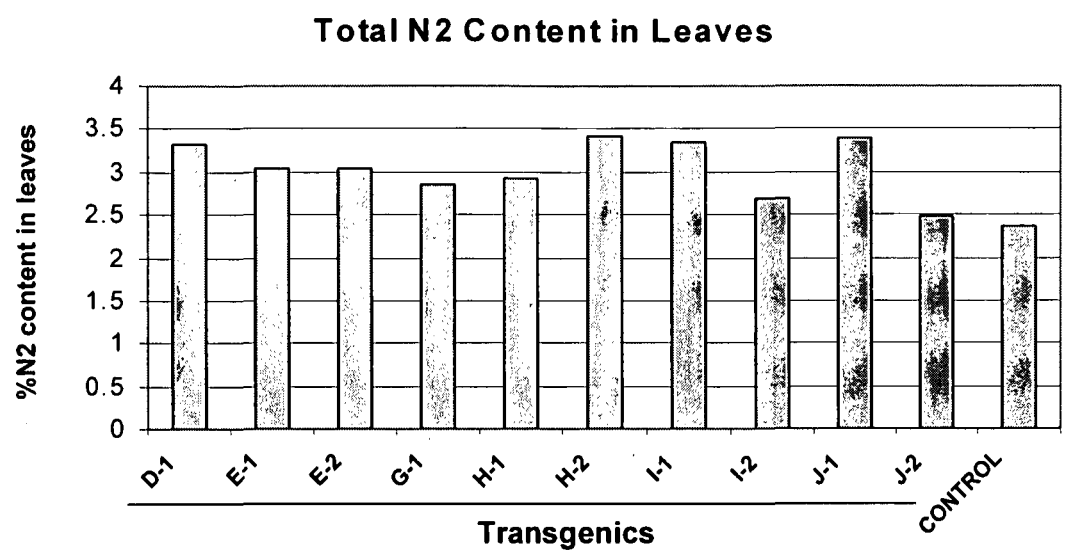
FIG. 5 shows the total percent nitrogen content in the leaves of different transgenic plants in T0 generation compared with the control plant.

All the 10 transgenics showed higher levels of N content as compared to the control (FIG. 5). The highest N content was observed in H2 (3.4%), which was 41% more than the wild type. The least increase in the N content was observed in J2 (2.5%), which was 4.1% more than the wild type. Thus the T0 transgenics with GAD gene showed an increased N content as compared to the wild type (with out the GAD transgene) when grown in soil with similar nutrient content.

The nitrogen uptake was further studied in the next generation (T1) to determine if the character is stable over generations. The experiments were conducted to study the effect both at seedling stage as well as during the whole life cycle of the plant.

Example 3

Evidence that the GAD Transgenic Plants Show a Better N Status in T1 Generation

To study the effect of different levels of nitrogen in the growth media on the transgenics two different sources of nitrogen were used—ammonium nitrate and potassium nitrate at 2, 4 and 8 mM concentrations, while not changing the levels of other nutrients (P and K) or micronutrients in the growth media.

Plant Material

T1 transgenic tobacco GAD plants were analyzed for their nitrogen status under different sources of nitrogen (Ammonium nitrate and Potassium nitrate).

The T1 seeds were sown on petri plates with hygromycin and the positive plants were taken ahead for further studies in green house like N2 uptake study with different levels of nitrogen.

Plant N-Status Under Different Levels of Ammonium Nitrate

T1 Seedling from three GAD transgenics (D1A, E2 and H1) which survived on hygromycin treated media were picked up and transplanted in small cups in the green house supplemented with $1/10^{th}$ MS media without N source. N was provided separately at different concentrations of Ammonium nitrate (2, 4 and 8 mM) and were compared with the wild type for the chlorophyll content. Readings were taken using a Minolta SPAD meter and expressed as SPAD units (FIG. 6). As the level of nitrogen in the growth media was reduced the wild type plants showed a decreased level of plant N content an indicator of N deficiency for its growth. However the transgenic plants did show a slight reduction in the plant N status under lower nitrogen availability but the N content was higher than the wild type plants indicating a better growth status compared to the wild type.

Plant N-Status Under Different Levels of Potassium Nitrate

T1 Seedling from three GAD transgenics (D1A, E2 and H1) which survived on hygromycin treated media were picked up and transplanted in small cups in the green house supplemented with $1/10^{th}$ MS media without N source. N was provided separately at different concentrations of Potassium nitrate (2, 4 and 8 mM) and were compared with the wild type for the chlorophyll content. Readings were taken using a Minolta SPAD meter and expressed as SPAD units (FIG. 7). The transgenic plants showed a higher plant N content as compared to the wild type in all the different concentrations of potassium nitrate indicating a better nitrogen uptake as compared to the wild type.

The transgenic plants with GAD gene showed a better plant N status under different sources of nitrogen supplied as well as under N deficient conditions.

Example 4

Evidence that the GAD Transgenic Plants Show a Better Nitrogen Use Efficiency (NUE) and Higher Harvest Index Under N Deficient Soil Conditions To study the effect of different levels of nitrogen in the soil on the growth and development of the transgenics different levels of nitrogen were used—100% recommended dose 50% recommended dose and 10% recommended dose, while not changing the levels of other nutrients (P and K) or micronutrients in the soil. Different levels of N were supplied externally by applying either urea or calcium ammonium nitrate (CAN) or Di-Ammonium phosphate (DAP).

The experiments were performed with the wild type and transgenic tobacco. T1 Seedling from three GAD transgenic (H1) which survived on hygromycin treated media were picked up and transplanted in small cups in the green house Seedlings were cultivated in a green house in pots containing mixture of field soil and farm yard manure (FYM). Plants were irrigated with normal water, with external application of fertilizers the fertilizer schedule is described in Table 1. The experiments were performed with three treatments and three replications with two genotypes (wild type and H1 transgenic tobacco) Table 2. The required dosage of fertilizers was calculated as below and actual dosage using different fertilizers is indicated in Tables 3, 4 and 5.

Fertilizer Application for GAD Transgenic Tobacco
  Recommended N dose for FCV tobacco 20 Kg N/Ha
  Recommended N dose for Bidi Tobacco 180 Kg N/Ha
  For loamy soils @ 60 Kg N, 80 Kg P2O5, 80-100 Kg K2O and 15 Kg MgO/ha
  For sandy soils, 70 Kg N, 60 Kg P2O5, 100-120 Kg K2O and 15 Kg MgO/ha are recommended.

TABLE 1 fertilizer schedule for tobacco plants when straight fertilizers are to be applied

| | |
|---|---|
| 1st split | 100% P2O5, 50% K2O and 25% of total N should be applied by band or dollop method 10 cm away from the plant 10 days after planting. |
| 2nd split | 50% of N and the remaining K2O along with 15 Kg MgO (100 Kg dolomite) to be applied 3-4 weeks after planting 10 cm away from the plant. Dolomite should not be applied along with phosphatic fertilizer. |
| 3rd split | Remaining 25% of N to be applied 40 days after planting by dollop method before ridging. |

Planting density of 10,000-12,000 seedlings/Ha is recommended for tobacco cultivation thus 1 seedling/m$^2$ (1 Ha=10,000 m$^2$) therefore the recommended dose of N per plant would be 6 gms N per seedlings (60,000 gms N per Ha (10,000 m$^2$) ie. Per 10,000 seedlings). Thus the dosage of using different fertilizers was calculated as below.

Urea (46% N Content):
  Urea fertilizer (46% N) ie. 46 Kg N/100 Kg urea (4.6 gms N/10 gms Urea)
  13 gms Urea per plant (will supply 6 gms N per plant as per recommended dose)
    25% first dose (3.25 gms Urea) (10 DAT)
    50% second dose (6.5 gms Urea) (2-3 weeks DAT)
    25% third dose (3.25 gms Urea) (40 DAT)

CAN (25% N Content):
  60,000 gms N per Ha (10,000 m$^2$) ie. Per 10,000 seedlings
  6 gms N per seedlings (recommended dose)
  CAN fertilizer (25% N) ie. 25 Kg N/100 Kg CAN (2.5 gms N/10 gms CAN)
  25 gms CAN per plant (will supply 6 gms N per plant as per recommended dose)
    25% first dose (6.25 gms CAN) (10 DAT)
    50% second dose (12.5 gms CAN) (2-3 weeks DAT)
    25% third dose (6.25 gms CAN) (40 DAT)

SSP (18% P$_2$O$_5$ Content):
  80,000 gms P$_2$O$_5$ per Ha (10,000 m$^2$) ie. Per 10,000 seedlings
  8 gms P$_2$O$_5$ per seedlings (recommended dose)
  SSP fertilizer (18% P$_2$O$_5$) ie. 18 Kg P$_2$O$_5$/100 Kg SSP (1.8 gms N/10 gms SSP)
  44.5 gms SSP per plant (will supply 8 gms P$_2$O$_5$ per plant as per recommended dose)
    100% first dose (44.5 gms SSP) (10 DAT)

DAP: (18% N and 46% P Content)
  80,000 gms P$_2$O$_5$ per Ha (10,000 m$^2$) ie. Per 10,000 seedlings
  8 gms P$_2$O$_5$ per seedlings (recommended dose)
  DAP fertilizer (46% P$_2$O$_5$) ie. 46 Kg P$_2$O$_5$/100 Kg SSP (4.6 gms N/10 gms DAP)
  17.4 gms DAP per plant (will supply 8 gms P$_2$O$_5$ per plant as per recommended dose)
    100% first dose (17.4 gms DAP) (10 DAT)

This will also supply 3.1 gms N where as recommended dose is 6 gms/seedling) ie. Need to supplement 3 gms through urea.
  Urea fertilizer (46% N) ie. 46 Kg N/100 Kg urea (4.6 gms N/10 gms Urea)
  6.5 gms Urea per plant (will supply 3 gms N per plant which is half of recommended dose)
    First dose (no urea if giving DAP) (10 DAT)
    25% second dose (3.25 gms Urea) (2-3 weeks DAT)
    25% third dose (3.25 gms Urea) (40 DAT)

MOP (60% K$_2$O Content):
  100,000 gms K$_2$O per Ha (10,000 m$^2$) ie. Per 10,000 seedlings
  10 gms K$_2$O per seedlings (recommended dose)
  MOP fertilizer (60% K$_2$O) ie. 60 Kg K$_2$O/100 Kg MOP (6 gms K$_2$O/10 gms MOP)
  16 gms MOP per plant (will supply 10 gms K$_2$O per plant as per recommended dose)
    50% first dose (8 gms MOP) (10 DAT)
    50% second dose (8 gms MOP) (2-3 weeks DAT)

TABLE 2

Experimental design for Nitrogen uptake studies. Three treatments and three replications were taken for two genotypes for comparison.

| | Treatment-1 (100% RD) | | Treatment-2 (50% RD) | | Treatment-1 (10% RD) | |
|---|---|---|---|---|---|---|
| Replication-1 | WT | H1 | WT | H1 | WT | H1 |
| Replication-2 | WT | H1 | WT | H1 | WT | H1 |
| Replication-3 | WT | H1 | WT | H1 | WT | H1 |

TABLE 3

If using Urea, SSp and MOP as fertilizers then the below dosage was followed

| | 100% RD gms/plant | 50% RD gms/plant | 10% RD gms/plant |
|---|---|---|---|
| UREA | 13 | 6.5 | 1.3 |
| SSP (P$_2$O$_5$) | 44.5 | 22.25 | 4.45 |
| MOP (K$_2$O) | 16 | 8 | 1.6 |

TABLE 4

If using Urea, DAP and MOP as fertilizers then the below dosage was followed

| | 100% RD gms/plant | 50% RD gms/plant | 10% RD gms/plant |
|---|---|---|---|
| UREA | 6.5 | 3.25 | 1.3 |
| DAP (N: P$_2$O$_5$) | 17.4 | 8.7 | 1.74 |
| MOP (K$_2$O) | 16 | 8 | 1.6 |

TABLE 5

If using CAN, SSP and MOP as fertilizers then the below dosage was followed.

| | 100% RD gms/plant | 50% RD gms/plant | 10% RD gms/plant |
|---|---|---|---|
| CAN | 25 | 12.5 | 2.5 |
| SSP (P$_2$O$_5$) | 44.5 | 22.25 | 4.45 |
| MOP (K$_2$O) | 16 | 8 | 1.6 |

Phenotypic Evaluation:

The phenotypic characters were observed and parameters like plant height, internodal distance, number of branches, number of leaves, leaf area, stem thickness (girth), total biomass, grain yield etc were recorded.

Plant Height

The height of the plant was measured in the transgenic plants and the wild type plants (plants with out the introduced glutamate decarboxylase gene). The plant height was measured using scale from the soil level to the tip of the plant including the inflorescence and the branches. The transgenic showed an increase in plant height at lower levels of soil N (10% RD) (FIG. 8).

Internodal Distance

The distance between two internodes on the stem was measured in the transgenic plants and the wild type plants (plants with out the introduced glutamate decarboxylase gene). The internodal distance was measured between the $5^{th}$ & $6^{th}$ leaf and $6^{th}$ & $7^{th}$ leaf. The leaf was counted from the top with the fully expanded leaf considered to be leaf number-1. The distance was measured using a thread and then measuring the thread length on a scale and expressed in cms. The transgenic showed an increase in internodal distance at lower levels of soil N (10% RD) (FIG. 9).

Number of Branches

The transgenic showed an increase in number of branches at sufficient soil N conditions (100% RD) and as well as deficient soil N conditions (50% RD) (FIG. 10).

Number of Leaves

The increase in number of leaves under sufficient soil N conditions (100% RD) was nearly two fold in the transgenic when compared to wild type. While under deficient soil N conditions (50% and 10% RD) also the transgenics were observed to have more number of leaves than the wild type plants (FIG. 11).

Stem Girth (Circumference or Stem Thickness)

The thickness of the stem was measured in the transgenic plants and the wild type plants (plants with out the introduced glutamate decarboxylase gene). Girth of the stem was measured at a height of 5-6 cms above from the soil level. A thread was used to circle the stem at the appropriate height and then the length of the thread was measured on a scale and expressed in cms. The transgenics showed a thicker stem under 100% RD conditions while no significant difference in stem thickness was observed under 50% and 10% RD condition (FIG. 12)

Leaf Area

The size of the leaf was measured in the transgenic plants and the wild type plants (plants with out the introduced glutamate decarboxylase gene). The leaf was measured vertically from the node to the tip of the leaf and was considered as the length of the leaf. The breadth of the leaf was measured horizontally at the broadest point and was considered as the breadth of the leaf. The leaf area was calculated as the Length×Breadth expressed in $cm^{-2}$ units. Under sufficient soil N conditions (100% RD) there was not difference in the leaf area between the transgenics and the wild type while under deficient soil N conditions (50% and 10% RD) the transgenics showed an increase in leaf area as compared to the wild type (FIG. 13).

Plant Biomass

The biomass generated was measured in the transgenic plants and the wild type plants (plants with out the introduced glutamate decarboxylase gene). Plant biomass was estimated as the total plant dry weight. The plant biomass was estimated under different nitrogen treatments. The total biomass from the transgenics was significantly higher ($P \leq 0.005$) as compared to the wild types in both N sufficient (100% RD) and N deficient (50% RD) conditions (FIG. 14).

Net Nitrogen Uptake

Total nitrogen uptake (% dry weight of leaves) by the plants was estimated. The net uptake was compared between the control and the transgenic plants under normal as well as different environmental stress conditions.

Nitrogen Estimation in T1 Plants

Analysis of T1 GAD tobacco plants along with the wild type was done for the nitrogen content in the leaves. The leaves were collected from mature plants and dried in hot air oven. The dried leaves were powdered and the $N_2$ content was estimated using Kjeldahl method as described earlier. The total plant N content from the transgenics was significantly higher ($P \leq 0.005$) as compared to the wild types in N sufficient (100% RD) conditions while under N deficient (50% and 10% RD) conditions there was no significant difference in the plant N content between the wild type and transgenics (FIG. 15).

Nitrogen Use Efficiency (NUE)

The Nitrogen Use Efficiency (NUE) was calculated as follows

Nitrogen use efficiency is expressed as the quantity of dry matter produced per unit of N present in the tissue.

A nutrient efficiency value can be derived from the N content of leaf tissue by the equation:

$$N \text{ use efficiency (mg dry matter/mg } N) = \frac{1000}{\text{mg } N/\text{g dry wt.}}$$

Or

NUE=Total Biomass(Dry weight in mg)/Amount of $N$ in biomass(in mg)

Or

NUE=Biomass produced/Nitrogen applied to the soil

Photosynthetic N use efficiency is defined as the $CO_2$ fixed per unit of N in a unit leaf area or leaf mass.

The nitrogen use efficiency (a factor of total biomass and the N content in the biomass) of the transgenics was higher as compared to the wild types in N deficient (50% RD) conditions (FIG. 16).

Grain Yield

The total grain yield was higher in the transgenics than the wild type under both N sufficient (100% RD) and N deficient (10% RD) conditions (FIG. 17). This indicates that the increased biomass is in fact also contributing towards the increased yield of the plants and there is no yield penalty due to increase in the biomass.

The GAD transgenics performed better than the wild type plants under N deficient conditions for the different agronomic and nutrient status of the plants thus indicating the role of GAD gene for the superior performance of the transgenics under N deficient conditions. This could be due to the increase uptake or assimilation of the applied N by the transgenics than the wild types.

We claim:

1. A method for increasing nitrogen content or nitrogen use efficiency of a plant, comprising: incorporating into a plant's genome a DNA construct comprising a promoter operably linked to a nucleotide sequence that encodes a functional glutamate decarboxylase (GAD) enzyme having the amino acid sequence set forth in SEQ ID NO:2 and cultivating said plant under low nitrogen conditions wherein nitrogen content or nitrogen use efficiency is increased in said plant as compared to a non-transformed plant cultivated under low nitrogen conditions.

2. The method according to claim 1, wherein the nucleotide sequence that encodes a functional glutamate decarboxylase enzyme comprises the nucleotide sequence set forth in SEQ ID NO:1.

3. The method according to claim 1, wherein the promoter is selected from the group consisting of a constitutive promoter, an inducible promoter, a tissue specific promoter, and a cell type specific promoter operably linked to the nucleotide sequence set forth in SEQ ID NO:1.

4. The method according to claim 3, wherein the inducible promoter responds to a signal selected from the group consisting of: mechanical shock, heat, cold, salt, flooding, drought, wounding, anoxia, pathogens, ultraviolet-B radiation, nutritional deprivation, a flowering signal, a fruiting signal, and cell specialization.

5. The method according to claim 3, wherein the tissue specific promoter expressed specifically in the tissues selected from the group consisting of: a leaf, a stem, a root, a flower, a petal, an anther, and an ovule.

6. The method according to claim 3, wherein promoter selected is from cell type specific promoter, expresses in plant cells selected from the group consisting of parenchyma, mesophyll, xylem, phloem, guard cell, and stomatal cell.

7. The method according to claim 1, wherein the transformed plant expresses glutamate decarboxylase (GAD) gene set forth in SEQ ID NO:1, at a higher level than the level of the GAD gene expressed by a non-transformed plant of the same species under the same conditions.

8. The method according to claim 1, wherein the plant is selected from the group consisting of monocots, dicots, cereals, forage crops, legumes, pulses, vegetables, fruits, oil seeds, fiber crops, flowers, horticultural, medicinal and aromatic plants.

9. The method of claim 1, wherein said incorporating DNA construct into plant genome comprises;
(i) transforming a cell, tissue or organ from a host plant with the DNA construct;
(ii) selecting a transformed cell, cell callus, somatic embryo, or seed which contains the DNA construct;
(iii) regenerating a whole plant from the selected transformed cell, cell callus, somatic embryo, or seed; and
(iv) selecting a regenerated whole plant that expresses the polynucleotide.

10. The method according to claim 1 wherein a cell tissue or organ from a host plant is transformed with the DNA construct mediated by a using particle gun, biolistics, or *Agrobacterium*.

11. The method according to claim 1 wherein the promoter is a 35S cauliflower mosaic virus promoter.

\* \* \* \* \*

SEQUENCE LISTING

<160> NUMBER OF SEQ ID NOS: 2

<210> SEQ ID NO 1
<211> LENGTH: 1479
<212> TYPE: DNA
<213> ORGANISM: Oryza sativa
<220> FEATURE:
<221> NAME/KEY: CDS
<222> LOCATION: (1)..(1479)

<400> SEQUENCE: 1

| | | | | | | | | | | | | | | | | |
|---|---|---|---|---|---|---|---|---|---|---|---|---|---|---|---|---|
| atg | gtg | ctc | tcc | aag | gcc | gtc | tcc | gag | agt | gac | atg | tcc | gtg | cac | tcc | 48 |
| Met | Val | Leu | Ser | Lys | Ala | Val | Ser | Glu | Ser | Asp | Met | Ser | Val | His | Ser | |
| 1 | | | | 5 | | | | | 10 | | | | | 15 | | |

| acc | ttc | gcc | tcc | cgc | tac | gtc | cgc | gcc | tcc | ctc | cca | agg | tac | cgg | atg | 96 |
|---|---|---|---|---|---|---|---|---|---|---|---|---|---|---|---|---|
| Thr | Phe | Ala | Ser | Arg | Tyr | Val | Arg | Ala | Ser | Leu | Pro | Arg | Tyr | Arg | Met | |
| | | | 20 | | | | | 25 | | | | | 30 | | | |

| ccg | gag | aac | tcg | atc | ccg | aag | gag | gcg | gcg | tac | cag | atc | atc | aac | gac | 144 |
|---|---|---|---|---|---|---|---|---|---|---|---|---|---|---|---|---|
| Pro | Glu | Asn | Ser | Ile | Pro | Lys | Glu | Ala | Ala | Tyr | Gln | Ile | Ile | Asn | Asp | |
| | | | 35 | | | | | 40 | | | | | 45 | | | |

| gag | ctg | atg | ctg | gac | ggc | aac | ccg | cgg | ctg | aac | ctg | gcg | tcg | ttc | gtc | 192 |
|---|---|---|---|---|---|---|---|---|---|---|---|---|---|---|---|---|
| Glu | Leu | Met | Leu | Asp | Gly | Asn | Pro | Arg | Leu | Asn | Leu | Ala | Ser | Phe | Val | |
| 50 | | | | | 55 | | | | | 60 | | | | | | |

| acc | acg | tgg | atg | gag | ccc | gag | tgc | gac | aag | ctc | atc | atg | gcc | gcc | atc | 240 |
|---|---|---|---|---|---|---|---|---|---|---|---|---|---|---|---|---|
| Thr | Thr | Trp | Met | Glu | Pro | Glu | Cys | Asp | Lys | Leu | Ile | Met | Ala | Ala | Ile | |
| 65 | | | | | 70 | | | | | 75 | | | | | 80 | |

| aac | aag | aac | tac | gtc | gac | atg | gac | gag | tac | ccc | gtc | acc | acc | gag | ctc | 288 |
|---|---|---|---|---|---|---|---|---|---|---|---|---|---|---|---|---|
| Asn | Lys | Asn | Tyr | Val | Asp | Met | Asp | Glu | Tyr | Pro | Val | Thr | Thr | Glu | Leu | |
| | | | | 85 | | | | | 90 | | | | | 95 | | |

| cag | aac | cgg | tgc | gtg | aac | atg | atc | gcg | cac | ctg | ttc | cac | gcg | ccg | ctc | 336 |
|---|---|---|---|---|---|---|---|---|---|---|---|---|---|---|---|---|
| Gln | Asn | Arg | Cys | Val | Asn | Met | Ile | Ala | His | Leu | Phe | His | Ala | Pro | Leu | |
| | | | 100 | | | | | 105 | | | | | 110 | | | |

| ggg | gag | gac | gag | acg | gcg | gtg | ggc | gtg | ggc | acg | gtg | ggt | tcg | tcg | gag | 384 |
|---|---|---|---|---|---|---|---|---|---|---|---|---|---|---|---|---|
| Gly | Glu | Asp | Glu | Thr | Ala | Val | Gly | Val | Gly | Thr | Val | Gly | Ser | Ser | Glu | |
| | | | 115 | | | | | 120 | | | | | 125 | | | |

| gcc | atc | atg | ctg | gcc | ggg | ctg | gcc | ttc | aag | cgg | cgg | tgg | cag | aac | aag | 432 |
|---|---|---|---|---|---|---|---|---|---|---|---|---|---|---|---|---|
| Ala | Ile | Met | Leu | Ala | Gly | Leu | Ala | Phe | Lys | Arg | Arg | Trp | Gln | Asn | Lys | |
| | | 130 | | | | | 135 | | | | | 140 | | | | |

| cgc | aag | gcc | gag | ggg | aag | ccg | ttc | gac | aag | ccc | aac | atc | atc | acc | ggc | 480 |
|---|---|---|---|---|---|---|---|---|---|---|---|---|---|---|---|---|
| Arg | Lys | Ala | Glu | Gly | Lys | Pro | Phe | Asp | Lys | Pro | Asn | Ile | Ile | Thr | Gly | |
| 145 | | | | | 150 | | | | | 155 | | | | | 160 | |

| gcc | aac | gtg | cag | gtg | tgc | tgg | gag | aag | ttc | gcc | cgc | tac | ttc | gag | gtg | 528 |
|---|---|---|---|---|---|---|---|---|---|---|---|---|---|---|---|---|
| Ala | Asn | Val | Gln | Val | Cys | Trp | Glu | Lys | Phe | Ala | Arg | Tyr | Phe | Glu | Val | |
| | | | | 165 | | | | | 170 | | | | | 175 | | |

| gag | ctc | aag | gag | gtg | aag | ctc | cgc | gac | ggc | tac | tac | gtc | atg | gac | ccc | 576 |
|---|---|---|---|---|---|---|---|---|---|---|---|---|---|---|---|---|
| Glu | Leu | Lys | Glu | Val | Lys | Leu | Arg | Asp | Gly | Tyr | Tyr | Val | Met | Asp | Pro | |
| | | | 180 | | | | | 185 | | | | | 190 | | | |

| gag | aag | gcc | gtc | gac | atg | gtc | aac | gag | aac | acc | atc | tgc | gtc | gcc | gcc | 624 |
|---|---|---|---|---|---|---|---|---|---|---|---|---|---|---|---|---|
| Glu | Lys | Ala | Val | Asp | Met | Val | Asn | Glu | Asn | Thr | Ile | Cys | Val | Ala | Ala | |
| | | | 195 | | | | | 200 | | | | | 205 | | | |

| atc | ctc | ggc | tcc | acc | ctc | aac | ggc | gag | ttc | gag | gac | gtc | aag | cta | ctc | 672 |
|---|---|---|---|---|---|---|---|---|---|---|---|---|---|---|---|---|
| Ile | Leu | Gly | Ser | Thr | Leu | Asn | Gly | Glu | Phe | Glu | Asp | Val | Lys | Leu | Leu | |
| | | 210 | | | | | 215 | | | | | 220 | | | | |

| aac | gac | ctc | ctc | gac | aag | aag | aac | aag | gag | act | ggg | tgg | gag | acg | ccg | 720 |
|---|---|---|---|---|---|---|---|---|---|---|---|---|---|---|---|---|
| Asn | Asp | Leu | Leu | Asp | Lys | Lys | Asn | Lys | Glu | Thr | Gly | Trp | Glu | Thr | Pro | |
| 225 | | | | | 230 | | | | | 235 | | | | | 240 | |

| atc | cac | gtg | gac | gcg | gcg | agc | ggc | ggg | ttc | atc | gcg | ccg | ttc | ctg | tac | 768 |
|---|---|---|---|---|---|---|---|---|---|---|---|---|---|---|---|---|
| Ile | His | Val | Asp | Ala | Ala | Ser | Gly | Gly | Phe | Ile | Ala | Pro | Phe | Leu | Tyr | |
| | | | | 245 | | | | | 250 | | | | | 255 | | |

-continued

| | | |
|---|---|---|
| ccg gag ctg gag tgg gac ttc cgg ctg ccg tgg gtg aag agc atc aac<br>Pro Glu Leu Glu Trp Asp Phe Arg Leu Pro Trp Val Lys Ser Ile Asn<br>260                         265                      270 | 816 |
| gtg agc ggt cac aag tac ggg ctc gtc tac gcc ggc atc ggc tgg tgc<br>Val Ser Gly His Lys Tyr Gly Leu Val Tyr Ala Gly Ile Gly Trp Cys<br>275                     280                      285 | 864 |
| atc tgg cgc aac aag gag gac ctg ccc gag gag ctc atc ttc cac atc<br>Ile Trp Arg Asn Lys Glu Asp Leu Pro Glu Glu Leu Ile Phe His Ile<br>290                       295                    300 | 912 |
| aac tac ctc ggc acc gac cag cca acc ttc acc ctc aac ttc tcc aag<br>Asn Tyr Leu Gly Thr Asp Gln Pro Thr Phe Thr Leu Asn Phe Ser Lys<br>305                       310                   315                320 | 960 |
| ggc tcc agc cag gtc atc gcc cag tac tac cag ctc atc cgc cac ggc<br>Gly Ser Ser Gln Val Ile Ala Gln Tyr Tyr Gln Leu Ile Arg His Gly<br>325                     330                    335 | 1008 |
| ttc gag ggg tac agg aac atc atg gag aac tgc cac gag aac gcg atg<br>Phe Glu Gly Tyr Arg Asn Ile Met Glu Asn Cys His Glu Asn Ala Met<br>340                     345                    350 | 1056 |
| gtg ctg aag gaa ggg ctg gtg aag acg ggg agg ttc gac atc gtg tcc<br>Val Leu Lys Glu Gly Leu Val Lys Thr Gly Arg Phe Asp Ile Val Ser<br>355                     360                    365 | 1104 |
| aag gac gaa ggg gtg ccg ctg gtg gcg ttc tcg ctc aag gac cgg agc<br>Lys Asp Glu Gly Val Pro Leu Val Ala Phe Ser Leu Lys Asp Arg Ser<br>370                     375                    380 | 1152 |
| cgg cac gac gag ttc gag atc tcc gac atg ctg cgc cgc ttc ggc tgg<br>Arg His Asp Glu Phe Glu Ile Ser Asp Met Leu Arg Arg Phe Gly Trp<br>385                     390                   395                400 | 1200 |
| atc gtg ccg gcg tac acc atg ccg ccc gac gcc cag cac gtc acg gtg<br>Ile Val Pro Ala Tyr Thr Met Pro Pro Asp Ala Gln His Val Thr Val<br>                   405                    410                    415 | 1248 |
| ctc cgc gtg gtc atc cgg gag gag ttc agc cgc acc ctc gcc gag cgc<br>Leu Arg Val Val Ile Arg Glu Glu Phe Ser Arg Thr Leu Ala Glu Arg<br>                   420                    425                    430 | 1296 |
| ctc gtc ctc gac atc gag aag gtg atg tac cag ctc gac gcg ctc ccc<br>Leu Val Leu Asp Ile Glu Lys Val Met Tyr Gln Leu Asp Ala Leu Pro<br>435                     440                    445 | 1344 |
| tcc agg ctc atg ccc ccc gtg ccg ccg gcg ccg ctg ctg gtg gtc gcc<br>Ser Arg Leu Met Pro Pro Val Pro Pro Ala Pro Leu Leu Val Val Ala<br>450                     455                    460 | 1392 |
| aag aag tcg gag ctc gag acg cag cgg tcg gtg acg gag gcg tgg aag<br>Lys Lys Ser Glu Leu Glu Thr Gln Arg Ser Val Thr Glu Ala Trp Lys<br>465                     470                   475                480 | 1440 |
| aag ttc gtg ctc gcc aag agg acc aac ggc gtc tgc tag<br>Lys Phe Val Leu Ala Lys Arg Thr Asn Gly Val Cys<br>                   485                    490 | 1479 |

<210> SEQ ID NO 2
<211> LENGTH: 492
<212> TYPE: PRT
<213> ORGANISM: Oryza sativa

<400> SEQUENCE: 2

Met Val Leu Ser Lys Ala Val Ser Glu Ser Asp Met Ser Val His Ser
1                 5                        10                      15

Thr Phe Ala Ser Arg Tyr Val Arg Ala Ser Leu Pro Tyr Arg Met
                   20                      25                      30

Pro Glu Asn Ser Ile Pro Lys Glu Ala Ala Tyr Gln Ile Ile Asn Asp
                 35                      40                      45

Glu Leu Met Leu Asp Gly Asn Pro Arg Leu Asn Leu Ala Ser Phe Val
50                   55                      60

```
Thr Thr Trp Met Glu Pro Glu Cys Asp Lys Leu Ile Met Ala Ala Ile
 65                  70                  75                  80

Asn Lys Asn Tyr Val Asp Met Asp Glu Tyr Pro Val Thr Thr Glu Leu
                 85                  90                  95

Gln Asn Arg Cys Val Asn Met Ile Ala His Leu Phe His Ala Pro Leu
            100                 105                 110

Gly Glu Asp Glu Thr Ala Val Gly Val Gly Thr Val Gly Ser Ser Glu
        115                 120                 125

Ala Ile Met Leu Ala Gly Leu Ala Phe Lys Arg Arg Trp Gln Asn Lys
    130                 135                 140

Arg Lys Ala Glu Gly Lys Pro Phe Asp Lys Pro Asn Ile Ile Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Arg Asp Gly Tyr Tyr Val Met Asp Pro
            180                 185                 190

Glu Lys Ala Val Asp Met Val Asn Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Asp Lys Lys Asn Lys Glu Thr Gly Trp Glu Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Trp Val Lys Ser Ile Asn
            260                 265                 270

Val Ser Gly His Lys Tyr Gly Leu Val Tyr Ala Gly Ile Gly Trp Cys
        275                 280                 285

Ile Trp Arg Asn Lys Glu Asp Leu Pro Glu Glu Leu Ile Phe His Ile
    290                 295                 300

Asn Tyr Leu Gly Thr Asp Gln Pro Thr Phe Thr Leu Asn Phe Ser Lys
305                 310                 315                 320

Gly Ser Ser Gln Val Ile Ala Gln Tyr Tyr Gln Leu Ile Arg His Gly
                325                 330                 335

Phe Glu Gly Tyr Arg Asn Ile Met Glu Asn Cys His Gly Asn Ala Met
            340                 345                 350

Val Leu Lys Glu Gly Leu Val Lys Thr Gly Arg Phe Asp Ile Val Ser
        355                 360                 365

Lys Asp Glu Gly Val Pro Leu Val Ala Phe Ser Leu Lys Asp Arg Ser
    370                 375                 380

Arg His Asp Glu Phe Glu Ile Ser Asp Met Leu Arg Arg Phe Gly Trp
385                 390                 395                 400

Ile Val Pro Ala Tyr Thr Met Pro Pro Asp Ala Gln His Val Thr Val
                405                 410                 415

Leu Arg Val Val Ile Arg Glu Glu Phe Ser Arg Thr Leu Ala Glu Arg
            420                 425                 430

Leu Val Leu Asp Ile Glu Lys Val Met Tyr Gln Leu Asp Ala Leu Pro
        435                 440                 445

Ser Arg Leu Met Pro Pro Val Pro Pro Ala Pro Leu Leu Val Val Ala
    450                 455                 460
```

-continued

```
Lys Lys Ser Glu Leu Glu Thr Gln Arg Ser Val Thr Glu Ala Trp Lys
465                 470                 475                 480

Lys Phe Val Leu Ala Lys Arg Thr Asn Gly Val Cys
                485                 490
```